US010300153B2

(12) United States Patent
Ichim et al.

(10) Patent No.: US 10,300,153 B2
(45) Date of Patent: May 28, 2019

(54) IMMUNOLOGICAL DETECTION OF ALTERED CELLS

(71) Applicant: Asthra, LLC, Pacific Palisades, CA (US)

(72) Inventors: Thomas Ichim, San Diego, CA (US); Santosh Kesari, Santa Monica, CA (US)

(73) Assignee: Asthra, LLC, Pacific Palisades, CA (US)

(*) Notice: Subject to any disclaimer, the term of this patent is extended or adjusted under 35 U.S.C. 154(b) by 116 days.

(21) Appl. No.: 15/365,677

(22) Filed: Nov. 30, 2016

(65) Prior Publication Data
US 2017/0151352 A1  Jun. 1, 2017

Related U.S. Application Data

(60) Provisional application No. 62/260,984, filed on Nov. 30, 2015.

(51) Int. Cl.
*A61K 49/00* (2006.01)
*A61K 51/12* (2006.01)

(52) U.S. Cl.
CPC ...... *A61K 49/0097* (2013.01); *A61K 49/0002* (2013.01); *A61K 51/1203* (2013.01)

(58) Field of Classification Search
None
See application file for complete search history.

(56) References Cited

U.S. PATENT DOCUMENTS

| | | |
|---|---|---|
| 5,268,486 A | 12/1993 | Waggoner |
| 6,027,709 A | 2/2000 | Little |
| 6,114,350 A | 9/2000 | Randall |
| 6,197,956 B1 | 3/2001 | Randall et al. |
| 6,224,644 B1 | 5/2001 | Randall |
| 6,437,141 B2 | 8/2002 | Randall |
| 6,649,335 B2 | 11/2003 | Missfeldt |
| 6,683,188 B1 | 1/2004 | Kasada |
| 6,995,274 B2 | 2/2006 | Lugade |

OTHER PUBLICATIONS

Abubakr, Y.A., T.H. Chou, and B.G. Redman, *Spontaneous remission of renal cell carcinoma: a case report and immunological correlates.* J Urol, 1994. 152(1): p. 156-7.
Albertini, M.R., et al., *Analysis of T cell receptor beta and gamma genes from peripheral blood, regional lymph node and tumor-infiltrating lymphocyte clones from melanoma patients.* Cancer Immunol Immunother, 1991. 32(5): p. 325-30.
Altenschmidt, U., E. Klundt, and B. Groner, *Adoptive transfer of in vitro-targeted, activated T lymphocytes results in total tumor regression.* J Immunol, 1997. 159(11): p. 5509-15.
Basilio-de-Oliveira, R.P. and V.L. Nunes Pannain, *Prognostic angiogenic markers (endoglin, VEGF, CD31) and tumor cell proliferation (Ki67) for gastrointestinal stromal tumors.* World J Gastroenterol, 2015. 21(22): p. 6924-30.
Bland, P.W., *The local immune response to large bowel tumors.* Acta Chir Scand Suppl, 1985. 525: p. 70-92.
Bodurtha, A.J., et al., *A clinical histologic, and immunologic study of a case of metastatic malignant melanoma undergoing spontaneous remission.* Cancer, 1976. 37(2): p. 735-42.
Bowles, A.P., Jr. and E. Perkins, *Long-term remission of malignant brain tumors after intracranial infection: a report of four cases.* Neurosurgery, 1999. 44(3): p. 636-42.
Bulkley, G.B., et al., *Long-term spontaneous regression of malignant melanoma with visceral metastases. Report of a case with immunologic profile.* Cancer, 1975. 36(2): p. 485-94.
Carpenito, C., et al., *Control of large, established tumor xenografts with genetically retargeted human T cells containing CD28 and CD137 domains.* Proc Natl Acad Sci U S A, 2009. 106(9): p. 3360-5.
Cole, W.H., *Relationship of causative factors in spontaneous regression of cancer to immunologic factors possibly effective in cancer.* J Surg Oncol, 1976. 8(5): p. 391-411.
Deng, Z., et al., *Adoptive T-cell therapy of prostate cancer targeting the cancer stem cell antigen EpCAM.* BMC Immunol, 2015. 16(1): p. 1.
Di Giorgio, A., et al., *The influence of tumor lymphocytic infiltration on long term survival of surgically treated colorectal cancer patients.* Int Surg, 1992. 77(4): p. 256-60.
Duff, S.E., et al., *CD105 is important for angiogenesis: evidence and potential applications.* FASEB J, 2003. 17(9): p. 984-92.
Ebato, M., et al., *Skewed distribution of TCR V alpha 7-bearing T cells within tumor-infiltrating lymphocytes of HLA-A24(9)-positive patients with malignant glioma.* Immunol Lett, 1993. 39(1): p. 53-64. Ferradini, L., et al., *Analysis of T cell receptor variability in tumor-infiltrating lymphocytes from a human regressive melanoma. Evidence for in situ T cell clonal expansion.* J Clin Invest, 1993. 91(3): p. 1183-90.
Firminger, H.I., *A pathologist looks at spontaneous regression of cancer.* Natl Cancer Inst Monogr, 1976. 44: p. 15-8.
Fisher, B., et al., *Tumor localization of adoptively transferred indium-111 labeled tumor infiltrating lymphocytes in patients with metastatic melanoma.* J Clin Oncol, 1989. 7(2): p. 250-61.
Goedegebuure, P.S., et al., *Adoptive immunotherapy with tumor-infiltrating lymphocytes and interleukin-2 in patients with metastatic malignant melanoma and renal cell carcinoma: a pilot study.* J Clin Oncol, 1995. 13(8): p. 1939-49.
Hamilton, D.H. and P.A. Bretscher, *Different immune correlates associated with tumor progression and regression: implications for prevention and treatment of cancer.* Cancer Immunol Immunother, 2008. 57(8): p. 1125-36.

(Continued)

*Primary Examiner* — Michail A Belyavskyi
(74) *Attorney, Agent, or Firm* — Knobbe, Martens, Olson & Bear LLP

(57) ABSTRACT

Disclosed are methods, compositions of matter, and protocols useful for the detection of altered cells in a patient. Immune cells capable of clonal expansion are engineered to produce a soluble signal upon activation and/or clonal expansion. The cells may possess a suicide gene, inducible upon administration pharmacological or light/radiation activatable, so as to eliminate the cells from body when desired. In another embodiment, immune cells produce a localized marker, the marker being visible with imaging technology. In other embodiments cells capable of non-clonal expansion are utilized. The disclosure provides means of utilizing the immunosurveillance properties of immune cells to diagnose and localize diseases associated with alteration of host cells.

16 Claims, No Drawings

(56) References Cited

OTHER PUBLICATIONS

Hayakawa, K., et al., *Study of tumor-infiltrating lymphocytes for adoptive therapy of renal cell carcinoma (RCC) and metastatic melanoma: sequential proliferation of cytotoxic natural killer and noncytotoxic T cells in RCC.* J Immunother (1991), 1991. 10(5): p. 313-25.
Hellstrom, K.E. and I. Hellstrom, *Spontaneous tumor regression: possible relationship to in vitro parameters of tumor immunity.* Natl Cancer Inst Monogr, 1976. 44: p. 131-4.
Hom, S.S., S.A. Rosenberg, and S.L. Topalian, *Specific immune recognition of autologous tumor by lymphocytes infiltrating colon carcinomas: analysis by cytokine secretion.* Cancer Immunol Immunother, 1993. 36(1): p. 1-8.
Hombach, A., et al., *A chimeric receptor that selectively targets membrane-bound carcinoembryonic antigen (mCEA) in the presence of soluble CEA.* Gene Ther, 1999. 6(2): p. 300-4.
Huang, F.Y., et al., *Bacterial surface display of endoglin by antigen 43 induces antitumor effectiveness via bypassing immunotolerance and inhibition of angiogenesis.* Int J Cancer, 2014. 134(8): p. 1981-90.
Hunt, M.J., et al., *Regression in basal cell carcinoma: an immunohistochemical analysis.* Br J Dermatol, 1994. 130(1): p. 1-8.
Hwu, P., et al., *In vivo antitumor activity of T cells redirected with chimeric antibody/T-cell receptor genes.* Cancer Res, 1995. 55(15): p. 3369-73.
Inoue, T., et al., *Spontaneous regression of merkel cell carcinoma: a comparative study of TUNEL index and tumor-infiltrating lymphocytes between spontaneous regression and non-regression group.* J Dermatol Sci, 2000. 24(3): p. 203-11.
Ishizu, H., et al., *Immune-mediated regression of 'metastatic' neuroblastoma in the liver.* J Pediatr Surg, 1994. 29(2): p. 155-9.
Jarosz, M., et al., *Therapeutic antitumor potential of endoglin-based DNA vaccine combined with immunomodulatory agents.* Gene Ther, 2013. 20(3): p. 262-73.
Jena, B., G. Dotti, and L.J. Cooper, *Redirecting T-cell specificity by introducing a tumor-specific chimeric antigen receptor.* Blood, 2010. 116(7): p. 1035-44.
Kawai, K., et al., *Enhancement of T cell proliferative response against autologous cancer cells of a metasatic renal cell carcinoma patient after unexplained regression.* Int J Urol, 2004. 11(12): p. 1130-2.
Kitai, H., et al., *Spontaneous regression of small cell lung cancer combined with cancer associated retinopathy.* Lung Cancer, 2015. 87(1): p. 73-6.
Knisely, T.L. and J.Y. Niederkorn, *Immunologic evaluation of spontaneous regression of an intraocular murine melanoma.* Invest Ophthalmol Vis Sci, 1990. 31(2): p. 247-57.
Kooi, S., et al., *Cytokine production by T-cell lines derived from tumor-infiltrating lymphocytes from patients with ovarian carcinoma: tumor-specific immune responses and inhibition of antigen-independent cytokine production by ovarian tumor cells.* Lymphokine Cytokine Res, 1993. 12(6): p. 429-37.
Kuppner, M.C., M.F. Hamou, and N. de Tribolet, *Immunohistological and functional analyses of lymphoid infiltrates in human glioblastomas.* Cancer Res, 1988. 48(23): p. 6926-32.
Lazarus, D.S., J.T. Kurnick, and R.L. Kradin, *Alterations in pulmonary function in cancer patients receiving adoptive immunotherapy with tumor-infiltrating lymphocytes and interleukin-2.* Am Rev Respir Dis, 1990. 141(1): p. 193-8.
Ma, D. and M.J. Gu, *Immune effect of tumor-infiltrating lymphocytes and its relation to the survival rate of patients with ovarian malignancies.* J Tongji Med Univ, 1991. 11(4): p. 235-9.
McGuinness, R.P., et al., *Anti-tumor activity of human T cells expressing the CC49-zeta chimeric immune receptor.* Hum Gene Ther, 1999. 10(2): p. 165-73.
Mentzer, S.J., *Immunoreactivity in lung cancer.* Chest Surg Clin N Am, 1995. 5(1): p. 57-71.
Minamoto, T., et al., *Medullary carcinoma with lymphocytic infiltration of the stomach. Clinicopathologic study of 27 cases and immunohistochemical analysis of the subpopulations of infiltrating lymphocytes in the tumor.* Cancer, 1990. 66(5): p. 945-52.
Murali, P.S., et al., *Interleukin-2 mediated regulation of mitogen-activated T cell reactivity from different lymphoid sources in patients with squamous cell carcinoma of the oral cavity.* J Oral Pathol Med, 1989. 18(6): p. 327-32.
Nakai, T., T. Shimomura, and F. Hirokawa, *Spontaneous regression of recurrent hepatocellular carcinoma after TAE: possible mechanisms of immune mediation.* Int J Clin Oncol, 2001. 6(3): p. 149-52.
Nakamura, Y., et al., *Spontaneous remission of a non-small cell lung cancer possibly caused by anti-NY-ESO-1 immunity.* Lung Cancer, 2009. 65(1): p. 119-22.
Oratz, R., et al., *Induction of tumor-infiltrating lymphocytes in human malignant melanoma metastases by immunization to melanoma antigen vaccine.* J Biol Response Mod, 1989. 8(4): p. 355-8.
Peoples, G.E., et al., *T-cell recognition of ovarian cancer.* Surgery, 1993. 114(2): p. 227-34.
Pisani, R.J., et al., *Lymphokine-activated killer (LAK) cell activity in tumor-infiltrating lymphocytes from non-small cell lung cancer.* Am J Clin Pathol, 1989. 92(4): p. 435-46.
Rosenberg, S.A., *The development of new cancer therapies based on the molecular identification of cancer regression antigens.* Cancer J Sci Am, 1995.1(2): p. 90-100.
Saleh, F., et al., *Direct evidence on the immune-mediated spontaneous regression of human cancer: an incentive for pharmaceutical companies to develop a novel anti-cancer vaccine.* Curr Pharm Des, 2005. 11(27): p. 3531-43.
Sawamura, Y. and N. de Tribolet, *Immunobiology of brain tumors.* Adv Tech Stand Neurosurg, 1990. 17: p. 3-64.
Skornick, Y., S. Topalian, and S.A. Rosenberg, *Comparative studies of the long-term growth of lymphocytes from tumor infiltrates, tumor-draining lymph nodes, and peripheral blood by repeated in vitro stimulation with autologous tumor.* J Biol Response Mod, 1990. 9(4): p. 431-8.
Steerenberg, P.A., et al., *Tumor infiltrating leukocytes (tils) during progressive tumor growth and BCG-mediated tumor regression.* Virchows Arch B Cell Pathol Ind Mol Pathol, 1990. 59(4): p. 185-94.
Svatek, R.S., et al., *Preoperative plasma endoglin levels predict biochemical progression after radical prostatectomy.* Clin Cancer Res, 2008. 14(11): p. 3362-6.
Topalian, S.L., D. Solomon, and S.A. Rosenberg, *Tumor-specific cytolysis by lymphocytes infiltrating human melanomas.* J Immunol, 1989. 142(10): p. 3714-25.
Topalian, S.L. and S.A. Rosenberg, *Tumor-infiltrating lymphocytes: evidence for specific immune reactions against growing cancers in mice and humans.* Important Adv Oncol, 1990: p. 19-41.
Tsujihashi, H., et al., *Immunocompetence of tissue infiltrating lymphocytes in bladder tumors.* J Urol, 1988. 140(4): p. 890-4.
Tsujihashi, H., et al., *Immunohistochemical detection of tissue-infiltrating lymphocytes in bladder tumors.* Urol Int, 1989. 44(1): p. 5-9.
Tsujihashi, H., et al., *Immunoresponse of tissue infiltrating lymphocytes in bladder tumors.* J Urol, 1989. 141(6): p. 1467-70.
Whiteside, T.L., *Cancer therapy with tumor-infiltrating lymphocytes: evaluation of potential and limitations.* In Vivo, 1991. 5(6): p. 553-9.
Wolf, G.T., et al., *Lymphocyte subpopulations infiltrating squamous carcinomas of the head and neck: correlations with extent of tumor and prognosis.* Otolaryngol Head Neck Surg, 1986. 95(2): p. 142-52.
Yoshino, I., et al., *Oligoclonal T lymphocytes infiltrating human lung cancer tissues.* Int J Cancer, 1991. 47(5): p. 654-8.
Zorn, E. and T. Hercend, *A MAGE-6-encoded peptide is recognized by expanded lymphocytes infiltrating a spontaneously regressing human primary melanoma lesion.* Eur J Immunol, 1999. 29(2): p. 602-7.

IMMUNOLOGICAL DETECTION OF ALTERED CELLS

CROSS-REFERENCE TO RELATED APPLICATIONS

The present Application claims the benefit of priority to U.S. Provisional Application No. 62/260,984, filed Nov. 30, 2015, which is hereby incorporated by reference in its entirety.

FIELD

Embodiments herein relate generally to the field of detecting altered cells, including cancer cells or diseased cells. Specifically, the disclosure includes immune activation being utilized as a means of diagnosing and detecting cancer, cancer metastasis, or diseased cells. The disclosure also includes utilization of tumor-recognizing immune cells that may be selectively killed by activation of a suicide gene for identification and localization of tumors.

BACKGROUND

Early diagnosis of cancer allows for interventions with higher likelihood of success. Unfortunately, for many tumors, markers that allow in vivo identification and localization do not exist. In some cancers, for example, in ovarian cancer, various cancer-associated antigens such as CA125, CA602, CA130, CA72-4, CA546, CA19-9, and STN are known tumor markers. Each of these tumor markers, however, is based on the difference in expression level, including an increase or decrease in protein expression level in serum between normal individuals and epithelial ovarian cancer patients. Such proteins are usually expressed in no small amount even in normal cells and therefore exhibit low specificity for epithelial ovarian cancer. Hence, these proteins produce high false-positive and false-negative rates and as such, are incapable of being used as high accuracy tumor markers. A tumor marker that contributes to the early detection of primary cancer still remains to be obtained.

SUMMARY

It is therefore an aspect of this disclosure to provide improved methods for detecting altered cells in an individual. It is a related aspect to provide improved detection of primary cancer.

Some embodiments disclosed herein relate to methods of detecting an altered cell in an individual. In some embodiments, the method includes the steps of obtaining a population of immune cells capable of activation subsequent to binding to one or a plurality of antigens on the altered cell, labeling the population of immune cells with a label capable of producing a detectable signal, administering to the individual the labeled population of immune cells, and detecting the altered cell with the labeled population of cells in vivo. In some embodiments, the altered cell is one or more of a preneoplastic cell, a neoplastic cell, a bacterially infected cell, a virally infected cell, a stressed cell, a diseased cell, or an autoimmune cell.

In some embodiments, the population of immune cells is autologous to the recipient. In some embodiments, the population of immune cells is allogeneic to the recipient. In some embodiments, the immune cells is one or more of B cells, T cells, innate lymphoid cells, natural killer cells, natural killer T cells, gamma delta T cells, macrophages, monocytes, dendritic cells, neutrophils, myeloid derived suppressor cells, hematopoietic stem cells, or mesenchymal stem cells. In some embodiments, the population of immune cells is one or more of B cells, T cells, innate lymphoid cells, natural killer cells, natural killer T cells, gamma delta T cells, T regulatory cells, macrophages, monocytes, dendritic cells, neutrophils, myeloid derived suppressor cells.

In some embodiments, the antigen found on altered cells is an antigen associated with cellular proliferation, an antigen associated with cancer, an antigen associated with cells exposed to stressors, an antigen associated with viral infection, an antigen associated with bacterial infection, or the protein or peptide derivative of a tumor associated antigen. In some embodiments, the antigen is one or more of CA19-9, CA125, CLPP, 707-AP, AFP, ART-4, BAGE family, BING-4, CAGE, MAGE family, GAGE family, SAGE family, b-catenin/m, bcr-abl, Calcium-activated chloride channel 2, CTL-recognized antigen on melanoma (CAMEL), CAP-1, CEA, CASP-8, CDK/4, CDC-27, Cyp-B, Cyclin-B1, DAM-8, DAM-10, ecto vimentin EGFR, ELV-M2, ep-CAM, EphA3, ETV6, G250, Gp100, HAGE, HER-2/neu, HPV E6/E7, Immature laminin receptor, Mesothelin, EPV-E6, LAGE, hTERT, SAP-1, survivin, iCE, MART-1, tyrosinase, MUC-1, MC1-R, NY-ESO-1, PRAME, SSX-2, PSA, PSMA, SSEA, TAG-72, Ig, TCR, TEL/AML, XAGE family, IDH1 mutation, IDH2 mutation, IL13Rα2 mutation, epCAM or WT-1.

In some embodiments, the label capable of producing a detectable signal upon activation is a gene element which encodes a molecule or series of molecules that are secreted and can be detected in systemic circulation of the individual. In some embodiments, the gene element is activated by a promoter associated with activation of the population of immune cells. In some embodiments, the promoter is activated as a consequence of T cell receptor signal transduction when the population of immune cells is a T cell, as a consequence of B cell receptor signal transduction when the population of immune cells is a B cell, as a consequence of NK activator receptor when the population of immune cells is a NK cell, as a consequence of NKG2D when the population of immune cells is a NK cell, as a consequence activation of a receptor of a danger associated molecular pattern (DAMP), or as a consequence activation of a pathogen associated molecular pattern (PAMP). In some embodiments, the DAMP receptor is one or more of a toll like receptor (TLR), a receptor for advanced glycation end products (RAGE), a siglec receptor, a stimulator of interferon genes (STING), a retinoic acid-inducible gene I (RIG-I), a melanoma differentiation-associated gene 5 (MDA5), or a Toll-interleukin 1 receptor domain (TIR)-containing adapter molecule 1 (TICAM-1). In some embodiments, the PAMP receptor is one or more of a toll like receptor (TLR), a receptor for advanced glycation end products (RAGE), a siglec receptor, a stimulator of interferon genes (STING), retinoic acid-inducible gene I (RIG-I), a melanoma differentiation-associated gene 5 (MDA5),or a Toll-interleukin 1 receptor domain (TIR)-containing adapter molecule 1 (TICAM-1).

In some embodiments, the population of immune cells is immortalized. In some embodiments, the immune cell is tagged ex vivo with an agent allowing for in vivo localization. In some embodiments, the agent is one or more of indium-111, one or a plurality of quantum dots, or technetium-99. 14. In some embodiments, the agent is one or more of a radiolabel imaging agent, a therapeutic agent, or a diagnostic agent. In some embodiments the agent is one or more of $^{110}$In, $^{111}$In, $^{177}$Lu, $^{18}$F, $^{52}$Fe, $^{62}$Cu, $^{64}$Cu, $^{67}$Ga, $^{68}$Ga, $^{86}$Y, $^{90}$Y, $^{89}$Zr, $^{94}$Tc, $^{94m}$Tc, $^{99m}$Tc, $^{120}$I, $^{123}$I, $^{124}$I, $^{125}$I, $^{131}$I, $^{154}$Gd, $^{155}$Gd, $^{156}$Gd, $^{157}$Gd, $^{158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, or $^{83}$Se, or one or a plurality of quantum dots.

In some embodiments, the population of immune cells is engineered to express a molecule binding with sufficient affinity to the altered-cell associated protein in order to induce an activation event in the immune cell. In some embodiments, the immune cell is a chimeric antigen receptor T cell. In some embodiments, the molecule capable of binding with sufficient affinity to the one or plurality of antigens on the altered cell is a chimeric antigen receptor. In some embodiments, the label capable of producing a detectable signal upon activation of the population of immune cells is a gene element which encodes a molecule or series of molecules whereby the cells can be detected in systemic circulation of the individual. In some embodiments, the label includes a green fluorescent protein (GFP), including, for example, Aequoria victoria GFP, *Renilla muelleri* GFP, *Renilla reniformis* GFP, *Renilla ptilosarcus*, a blue fluorescent protein (BFP), a yellow fluorescent protein (YFP), a red fluorescent protein (RFP), a cyan fluorescent protein (CFP), an orange fluorescent protein (OFP). In some embodiments, the label is a reporter gene. In some embodiments, the reporter genes include, but are not limited to neomycin, phosphoro-transferase, chloramphenicol acetyl transferase, thymidine kinase, β-glucuronidase, aminoglycoside, phosphotransferase, hygromycin B, xanthine-guanine phosphoribosyl, luciferases (e.g., renilla, firefly, etc.), DHFR/methotrexate, β-galactosidase, alkaline phosphatase, turbo and tagRFP, and nuclear targeted versions of any of the aforementioned reporter genes.

Some embodiments provided herein relate to a method of detecting an altered cell in an individual. In some embodiments, the method includes obtaining a delivery vehicle. IN some embodiments, the delivery vehicle is one or more of B cells, T cells, innate lymphoid cells, natural killer cells, natural killer T cells, gamma delta T cells, T regulatory cells, macrophages, monocytes, dendritic cells, neutrophils, myeloid derived suppressor cells, mast cells, hematopoietic stem cells, fibroblasts, stromal vascular fraction, exosomes, endothelial progenitor cells, mesenchymal stem cells, pluripotent cell lines, or engineered nanoparticles. In some embodiments, the delivery vehicle is capable of activation subsequent to binding to one or a plurality of antigens on the altered cell. In some embodiments, the method includes labeling the delivery vehicle a label capable of producing a detectable signal, administering to the individual the labeled delivery vehicle, and detecting the altered cell with the labeled delivery vehicle in vivo. In some embodiments, the label is a fluorescent label, a radioactive label, a magnetic label, or a sonographic label.

Some embodiments provided herein relate to a nucleic acid encoding a fusion protein. In some embodiments, the nucleic acid includes a first sequence. In some embodiments, the first sequence encodes a protein for detection of altered cells. In some embodiments, the nucleic acid includes a second sequence. In some embodiments, the second sequence encodes a label. In some embodiments, the nucleic acid includes a third sequence. In some embodiments, the third sequence encodes a promoter. In some embodiments, the label includes a green fluorescent protein (GFP), including, for example, Aequoria victoria GFP, *Renilla muelleri* GFP, *Renilla reniformis* GFP, *Renilla ptilosarcus*, a blue fluorescent protein (BFP), a yellow fluorescent protein (YFP), a red fluorescent protein (RFP), a cyan fluorescent protein (CFP), an orange fluorescent protein (OFP). In some embodiments, the label is a reporter gene. In some embodiments, the reporter genes include, but are not limited to neomycin, phosphoro-transferase, chloramphenicol acetyl transferase, thymidine kinase, β-glucuronidase, aminoglycoside, phosphotransferase, hygromycin B, xanthine-guanine phosphoribosyl, luciferases (e.g., renilla, firefly, etc.), DHFR/methotrexate, β-galactosidase, alkaline phosphatase, turbo and tagRFP, and nuclear targeted versions of any of the aforementioned reporter genes.

In some embodiments, the promoter is an inducible promoter or a constitutive promoter. In some embodiments, the promoter is activated as a consequence of T cell receptor signal transduction when the immune cell is a T cell, as a consequence of B cell receptor signal transduction when the immune cell is a B cell, as a consequence of NK activator receptor when the immune cell is a NK cell, as a consequence of NKG2D when the immune cell is a NK cell, as a consequence activation of a receptor of a danger associated molecular pattern (DAMP), or as a consequence activation of a pathogen associated molecular pattern (PAMP). In some embodiments, the DAMP receptor is one or more of a toll like receptor (TLR), a receptor for advanced glycation end products (RAGE), a siglec receptor, a stimulator of interferon genes (STING), a retinoic acid-inducible gene I (RIG-I), a melanoma differentiation-associated gene 5 (MDA5), or a Toll-interleukin 1 receptor domain (TIR)-containing adapter molecule 1 (TICAM-1). In some embodiments, the PAMP receptor is one or more of a toll like receptor (TLR), a receptor for advanced glycation end products (RAGE), a siglec receptor, a stimulator of interferon genes (STING), retinoic acid-inducible gene I (RIG-I), a melanoma differentiation-associated gene 5 (MDA5), or a Toll-interleukin 1 receptor domain (TIR)-containing adapter molecule 1 (TICAM-1).

In some embodiments, the nucleic acid further encodes a fourth sequence. In some embodiments, the fourth sequence encodes a suicide gene. In some embodiments, the suicide gene allows for elimination of the immune cells once diagnosis and localization of the tumor has been performed. In some embodiments, the suicide gene is thymidylate synthase. In some embodiments, cell death is induced following administration of ganciclovir. In some embodiments, the suicide gene includes HSV1-TK coding sequences.

Some embodiments provided herein relate to a cell for fusion protein secretion. In some embodiments, the cell includes the nucleic acid as described herein. In some embodiments, the cell includes an expression vector. In some embodiments, the expression vector includes the nucleic acid as described herein. In some embodiments, the expression vector is RNA or DNA. In some embodiments, the nucleic acid includes a first sequences encoding a protein for the detection of altered cells, a second sequence, wherein the second sequence encodes a label, and a third sequence, wherein the third sequence encodes a promoter. In some embodiments, the cell is a B cell. In some embodiments, the cell is a CD5+ B cell or a CD5− B cell. In some embodiments, the cell is a naïve B cell or a memory B cell. In some embodiments, the cell is a T cell. In some embodiments, the cell is a CD8+ or a CD4+ cell. In some embodiments, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some embodiments, the cell is a CD4+ T helper lymphocyte cell that is selected from the group consisting of naïve CD4+ T-cells, central memory CD4+ T-cells, effector memory CD4+ T-cells, and bulk CD4+ T-cells. In some embodiments, the cell is a precursor T-cell.

In some embodiments, the cell is a CD28+ or a CD28− cell. In some embodiments, the cell is a memory T cell of naïve T cell. In some embodiments, the cell expresses CD3. In some embodiments, the cell is a T regulatory cell. In some embodiments, the cell expresses one or more of CD25, CTLA-4, or FoxP3. In some embodiments, the cell is a stem cell. In some embodiments, the cell is a hematopoietic stem cell or NK cell. In some embodiments, the cell is a neuronal stem cell. In some alternatives, the cell further includes a chimeric antigen receptor.

DETAILED DESCRIPTION

The disclosure provides for use of immune cells as markers for tumor detection in vivo. In one embodiment, T cells with specificity to cancer cells are engineered so as to express a detectable marker upon activation. The detectable marker, in one embodiment of the disclosure is luciferase, in situations where in vivo detection of the tumor, together with localization, is desired. In another embodiment of the disclosure, the T cells are engineered to express an enzyme whose substrate can be detected in circulation or biofluids. The disclosure relies on the amplification and clonal expansion of immune cells subsequent to activation for generation of a detectable signal. In one embodiment of the disclosure, immune cells are labeled with a radioactive agent that permits in vivo tracking. One such agent is Tc99, which is well known in the art and protocols are widely available.

Unless defined otherwise, all technical and scientific terms used herein have the same meaning as commonly understood by one of ordinary skill in the art to which the disclosure pertains.

As used herein, "a" or "an" may mean one or more than one.

"About" as used herein when referring to a measurable value is meant to encompass variations of ±20% or ±10%, more preferably ±5%, even more preferably ±1%, and still more preferably ±0.1% from the specified value.

As used herein, the term "suicide gene" refers to a nucleic acid encoding a product, wherein the product causes cell death by itself or in the presence of other compounds. Thus, a suicide gene refers to a gene, the expression of which in a host cell causes or results in a reduced viability of such host cells. In particular settings, the suicide gene will cause a cell to kill itself through apoptosis. In certain such settings, expression of the suicide gene will result in an enzyme, which catalyzes the generation of a cytotoxic drug from a non-toxic prodrug. Within the practice of the disclosure are envisioned suicide genes allowing for elimination of the immune cells once diagnosis and localization of the tumor has been performed. An example of a suicide gene is thymidylate synthase, which is known to induce cell death subsequent to administration of ganciclovir or valganciclovir (a prodrug formulation with improved oral bioavailability). In some embodiments, the suicide gene includes herpes simplex virus type 1 thymidine kinase (HSV1-TK) coding sequences.

As used herein, "cancer" refers to all types of cancer or neoplasm or malignant tumors found in animals, including leukemias, carcinomas and sarcomas. Examples of cancers are cancer of the brain, melanoma, bladder, breast, cervix, colon, head and neck, kidney, lung, non-small cell lung, mesothelioma, ovary, prostate, sarcoma, stomach, uterus and Medulloblastoma. The term "leukemia" is meant broadly progressive, malignant diseases of the hematopoietic organs/ systems and is generally characterized by a distorted proliferation and development of leukocytes and their precursors in the blood and bone marrow. Leukemia diseases include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophilic leukemia, blast cell leukemia, bovine leukemia, chronic myelocytic leukemia, leukemia cutis, embryonal leukemia, eosinophilic leukemia, Gross' leukemia, Rieder cell leukemia, Schilling's leukemia, stem cell leukemia, subleukemic leukemia, undifferentiated cell leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, and promyelocytic leukemi., The term "carcinoma" refers to a malignant new growth made up of epithelial cells tending to infiltrate the surrounding tissues, and/or resist physiological and non-physiological cell death signals and give rise to metastases. Exemplary carcinomas include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrmcous carcinoma, carcinoma villosum, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, and carcinoma scroti, The term "sarcoma" generally refers to a tumor which is made up of a substance like the embryonic connective tissue and is generally composed of closely packed cells embedded in a fibrillar, heterogeneous, or homogeneous substance. Sarcomas include, chondrosarcoma, fibrosarcoma, lymphosarcoma, melanosarcoma, myxosarcoma, osteosarcoma, endometrial sarcoma, stromal sarcoma, Ewing's sarcoma, fascial sarcoma, fibroblastic sarcoma, giant cell sarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilns' tumor sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma. Additional exemplary neoplasias include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, and adrenal cortical cancer.

In some particular embodiments of the disclosure, the cancer treated is a melanoma. The term "melanoma" is taken to mean a tumor arising from the melanocytic system of the skin and other organs. Melanomas include, for example, Harding-Passey melanoma, juvenile melanoma, lentigo maligna melanoma, malignant melanoma, acral-lentiginous melanoma, amelanotic melanoma, benign juvenile melanoma, Cloudman's melanoma, S91 melanoma, nodular melanoma subungal melanoma, and superficial spreading melanoma. In one embodiment, stressed cells are recognized by the modified immune cells of the disclosure. Stressed cells may be recognized by immune cells that selectively are activated in response to proteins associated with stress such as heat shock proteins. Conditions that the disclosure may be useful for diagnosing are selected from the group consisting of: motor-neuron disease, multiple sclerosis, degenerative diseases of the CNS, dementia, Alzheimer's Disease, Parkinson's Disease, cerebrovascular accidents, epilepsy, temporary ischaemic accidents, mood disorders, psychotic illness, specific lobe dysfunction, pressure related CNS injury, cognitive dysfunction, deafness, blindness, anosmia, motor deficits, sensory deficits, head injury, trauma to the CNS, arrhythmias, myocardial infarction, pericarditis, congestive heart disease, valve related pathologies, myocardial dysfunction, endocardial dysfunction, pericardial dysfunction, sclerosis and thickening of valve flaps, fibrosis of cardiac muscle, decline in cardiac reserve, congenital defects of the heart or circulatory system, developmental defects of the heart or circulatory system, hypoxic or necrotic damage, blood vessel damage, cardiovascular disease (for example, angina, dissected aorta, thrombotic damage, aneurysm, atherosclerosis, emboli damage), disorders of the sweat gland, disorders of the sebaceous gland, piloerectile dysfunction, follicular problems, hair loss, epidermal disease, disease of the dermis or hypodermis, burns, ulcers, sores, infections, striae, seborrhoea, rosacea, disorders of the musculoskeletal system including disease and damage to muscles and bones, endocondral ossification, osteoporosis, osteomalacia, rickets, pagets disease, rheumatism, arthritis, diseases of the endocrine system, diseases of the lymphatic system, diseases of the urinary system, diseases of the reproductive system, metabolic diseases, diseases of the sinus, diseases of the nasopharynx, diseases of the oropharynx, diseases of the laryngopharynx, diseases of the larynx, diseases of the ligaments, diseases of the vocal cords, vestibular folds, glottis, epiglottis, trachea, mucocilliary mucosa, trachealis muscles, emphysema, chronic bronchitis, pulmonary infection, asthma, tuberculosis, cystic fibrosis, diseases of gas exchange, burns, barotraumas, dental care, periodontal disease, deglutination problems, ulcers, enzymatic disturbances/deficiencies, fertility problems, paralysis, dysfunction of absorption or absorptive services, diverticulosis, inflammatory bowel disease, hepatitis, cirrhosis, portal hypertension, diseases of sight, and cancer.

As used herein, "immune cell" refers to a cell capable of interacting with a cell that has abnormal qualities. Immune cells may include cells classically known to play a role in the immune system, such as T cells, B cells, and NK cells, or cells that are not classically considered immune cells but play a role in the identification of pathology. The cells include mesenchymal stem cells, hematopoietic stem cells or progeny thereof, and monocytes. In some embodiments immune cells are autologous to the recipient, or in other embodiments immune cells are allogeneic. In some specific embodiments, allogeneic cells are used that possess reduced allogenicity. Immune cells can include, for example, B cells, T cells, innate lymphoid cells, natural killer cells, natural killer T cells, gamma delta T cells, T regulatory cells, macrophages, monocytes, dendritic cells, neutrophils, myeloid derived suppressor cells.

"Redirected immune cell" refers to an immune cell, which has been modified to specifically recognize characteristics associated with an abnormal cell. In one specific example a "redirected immune cell" refers to a CAR-T cell, in another specific embodiment a "redirected immune cell refers to a cell made to express a non-endogenous receptor, wherein the non-endogenous receptor allows for a specific interaction with an abnormal cell.

As used herein, the term "population of immune cells" refers to one or more immune cells, such as a group of immune cells.

"Obtaining a population of immune cells" can be achieved by removal of a sample from a subject and purifying the population of immune cells. The population of immune cells may be obtained, for example, by obtaining a sample having a population of immune cells, including a blood sample, a tissue sample, or a biological fluid sample. The sample may be obtained by withdrawing blood or biological fluid from a subject or by removal of cells, tumors, or tissues from a subject.

As used herein, the term "delivery vehicle" refers to a molecule or composition useful for holding or suspending and transporting a compound in vivo for the purpose of localization and detection or release and delivery of the transported compound. Delivery vehicles can include, for example, B cells, T cells, innate lymphoid cells, natural killer cells, natural killer T cells, gamma delta T cells, T regulatory cells, macrophages, monocytes, dendritic cells, neutrophils, myeloid derived suppressor cells, mast cells, hematopoietic stem cells, fibroblasts, stromal vascular fraction, exosomes, endothelial progenitor cells, mesenchymal stem cells, pluripotent cell lines, or engineered nanoparticles. The delivery vehicle may be obtained by manufacture or by removal of a sample from a subject and purifying a delivery vehicle from the sample.

"Abnormal cell" or "altered cell" within the context of the current disclosure refers to a cell which is one or more of the following: neoplastic, preneoplastic, bacterially infected, virally infected, stressed, apoptotic, necrotic, autophagic, or subjected to an abnormal environment.

"Mesenchymal stem cell" or "MSC" refers to cells that are (1) adherent to plastic, (2) express CD73, CD90, and CD105 antigens, while being CD14, CD34, CD45, and HLA-DR negative, and (3) possess ability to differentiate to osteogenic, chondrogenic and adipogenic lineage. As used herein, "mesenchymal stromal cell" or "MSC" can be derived from any tissue including, but not limited to, bone marrow, adipose tissue, amniotic fluid, endometrium, trophoblast-derived tissues, cord blood, Wharton jelly, placenta, amniotic tissue, derived from pluripotent stem cells, and tooth. As used herein, "mesenchymal stromal cell" or "MSC" includes cells that are CD34 positive upon initial isolation from tissue but are similar to cells described about phenotypically and functionally. As used herein, "MSC" includes cells that are isolated from tissues using cell surface markers including, for example, NGF-R, PDGF-R, EGF-R, IGF-R, CD29, CD49a, CD56, CD63, CD73, CD105, CD106, CD140b, CD146, CD271, MSCA-1, SSEA4, STRO-1 and STRO-3 or any combination thereof, and satisfy the ISCT criteria either before or after expansion. As used herein, "mesenchymal stromal cell" or "MSC" includes cells described in the literature as bone marrow stromal stem cells (BMSSC), marrow-isolated adult multipotent inducible cells (MIAMI) cells, multipotent adult progenitor cells (MAPC), mesenchymal adult stem cells (MASCS), Multi-Stem®, Prochymal®, remestemcel-L, Mesenchymal Precursor Cells (MPCs), Dental Pulp Stem Cells (DPSCs), PLX cells, PLX-PAD, AlloStem®, Astrostem®, Ixmyelocel-T, MSC-NTF, NurOwn™, StemedyneTM-MSC, Stempeucel®, StempeucelCLI, StempeucelOA, HiQCell, Hearticellgram-AMI, Revascor®, Cardiorel®, Cartistem®, Pneumostem®, Promostem®, Homeo-GH, AC607, PDA001, SB623, CX601, AC607, Endometrial Regenerative Cells (ERC), adipose-derived stem and regenerative cells (ADRCs). In some embodiments, MSC are used as "immune cells."

As used herein, the term "antigen" refers to a biomolecule that binds specifically to the respective antibody. An antibody from the diverse repertoire binds a specific antigenic structure by means of its variable region interaction (CDR loops). An antigen can be any natural or synthetic immunogenic substance, such as a protein, peptide, or hapten and include, for example, infectious tumor antigens, against which protective or therapeutic immune responses are desired. Antigens can include, for example, any antigen associated with a diseased cell, cancer cell, stressed cell, or an antigen of interest. Such antigens may include, for example, CA19-9, CA125, CLPP, 707-AP, AFP, ART-4, BAGE family, BING-4, CAGE, MAGE family, GAGE family, SAGE family, b-catenin/m, bcr-abl, Calcium-activated chloride channel 2, CTL-recognized antigen on melanoma (CAMEL), CAP-1, CEA, CASP-8, CDK/4, CDC-27, Cyp-B, Cyclin-B1, DAM-8, DAM-10, ecto vimentin EGFR, ELV-M2, ep-CAM, EphA3, ETV6, G250, Gp100, HAGE, HER-2/neu, HPV E6/E7, Immature laminin receptor, Mesothelin, EPV-E6, LAGE, hTERT, SAP-1, survivin, iCE, MART-1, tyrosinase, MUC-1, MC1-R, NY-ESO-1, PRAME, SSX-2, PSA, PSMA, SSEA, TAG-72, Ig, TCR, TEL/AML, XAGE family, IDH1 mutation, IDH2 mutation, IL13Rα2 mutation, epCAM, or WT-1.

As used herein, the term "detectable signal" refers to a signal from a molecule that may be detected. The molecule that provides the signal is referred to as a detectable molecule or label. A number of suitable labels include polypeptides. As such, as used herein, a "label nucleic acid" refers to a nucleic acid encoding a label. The detectable signal may include fluorescent label, a radioactive label, a magnetic label, or a sonographic label. Example labels that are suitable in accordance with embodiments herein include, but are not limited to, green fluorescent protein (GFP), including, for example, Aequoria victoria GFP, Renilla muelleri GFP, Renilla reniformis GFP, Renilla ptilosarcus, blue fluorescent protein (BFP), yellow fluorescent protein (YFP), red fluorescent protein (RFP), cyan fluorescent protein (CFP), orange fluorescent proteins (OFP). Additional reporter genes include, but are not limited to neomycin, phosphoro-transferase, chloramphenicol acetyl transferase, thymidine kinase, luciferase, β-glucuronidase, aminoglycoside, phosphotransferase, hygromycin B, xanthine-guanine phosphoribosyl, luciferases (e.g., renilla, firefly, etc.), DHFR/methotrexate, β-galactosidase, alkaline phosphatase, turbo and tagRFP, and nuclear targeted versions of any of the aforementioned reporter genes. In some embodiments, the polypeptide of interest includes the label itself, for example when production of label in active cells is desired.

As used herein, the term "activation" refers to an increase in immune cell function, for example, the release of cytokines, antibodies, and/or the induction of apoptosis following stimulation with one or more stimulatory molecules. Thus, "activation" or "activating" refers to the stimulation of a B cell, T cell, or any immune effector cell, to proliferate and/or differentiate. Thus, for example, an "activated B cell" refers to a B cell that has been signaled to proliferate and/or differentiate. Also, for example, an "activated T cell" refers to a T cell that has been signaled to proliferate and/or differentiate. This is in contrast to a naive B cell, which is typically quiescent. Those of skill in the art will be familiar with methods of identifying an activated B cell. One method is to simply observe the proliferation of the activated B cells. Other approaches include assessing the expression of one or more molecules, such as co-stimulatory molecules (e.g., CD80, CD86) or adhesion molecules (e.g., ICAM-I), that are up-regulated in activated B cells. Similar analysis of other effector cells can be made to determination their activation via the methods of the present disclosure.

As used herein, the term "localization" refers to direction of a molecule to a specific cell, tissue, organelle, or intracellular region.

As used herein, the term "fusion" or "fused" refers to a first nucleic acid linked to a second nucleic acid by a phosphodiester bond, so that a coding sequence at the 3' end of the first nucleic acid is in frame with a coding sequence at the 5' end of the second nucleic acid, and by extension can further refer to a first polypeptide linked by a peptide bond to a second polypeptide at the C-terminus of the first polypeptide. As such, a "fused" (or "fusion of a") nucleic acid or peptide as used herein refers to a configuration of molecules, and does not necessarily involve performing the act of joining two molecules together. By way of example, the fusion of the first nucleic acid to the second nucleic acid can encode a single polypeptide in which a first polypeptide sequence (encoded by the first nucleic acid) is fused to a second polypeptide sequence (encoded by the second nucleic acid). In some embodiments, the molecule including the fused nucleic acids is referred to as a fusion nucleic acid.

"Coding for" or "encoding" are used herein, and refers to the property of specific sequences of nucleotides in a polynucleotide, such as a gene, a cDNA, or an mRNA, to serve as templates for synthesis of other macromolecules such as a defined sequence of amino acids. Thus, a gene codes for a protein if transcription and translation of mRNA corresponding to that gene produces the protein in a cell or other biological system.

A "nucleic acid sequence coding for a polypeptide" includes all nucleotide sequences that are degenerate versions of each other and that code for the same amino acid sequence. In some alternatives, a nucleic acid is provided, wherein the nucleic acid encodes a fusion protein.

"Vector," "Expression vector" or "construct" is a nucleic acid used to introduce heterologous nucleic acids into a cell that has regulatory elements to provide expression of the heterologous nucleic acids in the cell. Vectors include but are not limited to viruses, plasmid, minicircles, yeast, cosmids, and phages. In some alternatives, the vector is a viral vector. In some alternatives, the viral vector is a lentivirus. In some alternatives, the vector is for protein expression in a bacterial system such as E. coli. Typically, a vector is a plasmid or a virus, used to transmit genetic material to a host cell. Vectors are preferably capable of autonomous replication. Typically, an expression vector includes a transcription promoter, a gene, and a transcription terminator. Gene expression is usually placed under the control of a promoter, and a gene is "operably linked to" the promoter.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

"Nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which include naturally-occurring or modified nucleic acid bases attached to a polyamide backbone. Nucleic acids can be either single stranded or double stranded. In some alternatives, a nucleic acid sequence encoding a fusion protein is provided. In some alternatives, the nucleic acid is RNA or DNA.

As used herein, the term "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A promoter can be inducible, repressible, and/or constitutive. Inducible promoters initiate increased levels of transcription from DNA under their control in response to some change in culture conditions, such as a change in temperature.

"Conditional" or "inducible" as used herein refers to a nucleic acid construct that includes a promoter that provides for gene expression in the presence of an inducer and does not substantially provide for gene expression in the absence of the inducer. Without being limiting, examples of inducible promoters for mammalian expression constructs include tetracycline, ecdysone, streptogramins, macrolides or doxycycline inducible promoters. In some alternatives, wherein a nucleic acid encoding a fusion protein is provided, the nucleic acid further includes a promoter sequence. In some alternatives, the promoter is an inducible promoter. In some alternatives, the promoter is an inducible promoter for expression in a mammalian system. In some alternatives, wherein the promoter is an inducible promoter for mammalian expression, the inducible promoter is a tetracycline, ecdysone, streptogramins, macrolides or doxycycline inducible promoter. In some alternatives, wherein the promoter is for mammalian cell protein expression, the promoter is regulated by a drug. In some alternatives, wherein the promoter is for mammalian cell protein expression, the promoter is regulated by a CAR-dependent signal. In some alternatives, an inducible promoter is designed and/or modified to provide for a low level of basal activity, a high level of inducibility, and/or a short time for reversibility.

"Constitutive" as used herein refers to the nucleic acid construct that includes a promoter that is constitutive, and thus provides for expression of a polypeptide that is continuously produced. In some alternatives, an affective amount of the drug for inducing expression is an amount that provides for an increase in transgene expression over uninduced and/or basal level of expression. In some alternatives, this amount can be readily determined using known dosages and pharmacokinetic profile of the drug.

In some alternatives, the inducible promoter has a low level of basal activity. In some alternatives, wherein a lentiviral vector is used, the level of basal activity in uninduced cells is 20%, 15%, 10%, 5%, 4%, 3%, 2%, 1% or less, as compared to when cells are induced to express the gene. The level of basal activity can be determined by measuring the amount of the expression of the transgene (e.g. marker gene) in the absence of the inducer (e.g. drug) using flow cytometry. In some alternatives, the inducible promoter provides for a high level of induced activity, as compared to uninduced or basal activity. In some alternatives, the level of activity in the induced state is 2, 4, 6, 8, or 10 fold or greater than the activity level in the uninduced state.

T-cells" or "T lymphocytes" as used herein can be from any mammalian, preferably primate, species, including monkeys, dogs, and humans. In some alternatives the T-cells are allogeneic (from the same species but different donor) as the recipient subject; in some alternatives the T-cells are autologous (the donor and the recipient are the same); in some alternatives the T-cells are syngeneic (the donor and the recipients are different but are identical twins).

As used herein, the term "subject," "individual," or "patient" is an animal, such as a vertebrate, preferably a mammal. The term "mammal" is defined as an individual belonging to the class Mammalia and includes, without limitation, humans, domestic and farm animals, and zoo, sports, or pet animals, such as sheep, dogs, horses, cats or cows. In some embodiments, the subject is mouse or rat. In some embodiments, the subject is human. A "subject" includes any animal that exhibits a symptom, or is at risk for exhibiting a symptom, of one or more disorder described herein. Suitable subjects (patients) include laboratory animals (such as mouse, rat, rabbit, or guinea pig), farm animals, and domestic animals or pets (such as a cat or dog). Non-human primates and, preferably, human patients, are included.

As used herein, the term "administration" includes intravenous administration or infusion. Thus, administration of labeled immune cells or administration of labeled delivery vehicles includes intravenous administration of the labeled compound to the subject, or infusion of the labeled compound. In some alternatives, administration includes reinfusion of the labeled immune cells or delivery vehicle, in the case where the immune cells or delivery vehicle was initially obtained from the subject, purified, labeled, and then reintroduced to the subject.

In one embodiment, loss of antigen is detected by immune cells generated to either produce, or stop producing a detectable signals subsequent to loss of antigen. The present disclosure relates to a strategy of adoptive cell transfer of T cells transduced to express a chimeric antigen receptor (CAR), which contain a single or plurality of markers useful for detection and localization of tumors. CARs are molecules that combine antibody-based specificity for a desired antigen (e.g., tumor endothelial antigen) with a T cell receptor-activating intracellular domain to generate a chimeric protein that exhibits a specific anti-tumor endothelium cellular immune activity. In one embodiment the present disclosure relates generally to the use of T cells genetically modified to stably express a desired CAR that possesses high affinity towards tumor associated endothelium. T cells expressing a CAR are referred to herein as CAR T cells or CAR modified T cells. Preferably, the cell can be genetically modified to stably express an antibody binding domain on its surface, conferring novel antigen specificity that is MHC independent. In some instances, the T cell is genetically modified to stably express a CAR that combines an antigen recognition domain of a specific antibody with an intracellular domain of the CD3-zeta chain or FcγRI protein into a single chimeric protein. In one embodiment, the CAR of the disclosure includes an extracellular domain having an antigen recognition domain, a transmembrane domain, and a cytoplasmic domain. In one embodiment, the transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex. Preferably, the transmembrane domain is the CD8α hinge domain. Numerous means of generating CAR-T cells are known in the art.

For example, Groner's group genetically modified T lymphocytes and endowed them with the ability to specifically recognize cancer cells. Tumor cells overexpressing the ErbB-2 receptor served as a model. The target cell recognition specificity was conferred to T lymphocytes by transduction of a chimeric gene encoding the zeta-chain of the TCR and a single chain antibody (scFv(FRP5)) directed against the human ErbB-2 receptor. The chimeric scFv (FRP5)-zeta gene was introduced into primary mouse T lymphocytes via retroviral gene transfer. Naive T lymphocytes were activated and infected by cocultivation with a retrovirus-producing packaging cell line. The scFv(FRP5)-zeta fusion gene was expressed in >75% of the T cells. These T cells lysed ErbB-2-expressing target cells in vitro with high specificity. In a syngeneic mouse model, mice were treated with autologous, transduced T cells. The adoptively transferred scFv(FRP5)-zeta-expressing T cells caused total regression of ErbB-2-expressing tumors. The presence of the transduced T lymphocytes in the tumor tissue was monitored. No humoral response directed against the transduced T cells was observed. Abs directed against the ErbB-2 receptor were detected upon tumor lysis (Altenschmidt, U., E. Klundt, and B. Groner, *Adoptive transfer of in vitro-targeted, activated T lymphocytes results in total tumor regression.* J Immunol, 1997. 159(11): p. 5509-15). Hombach et al. constructed an anti-CEA chimeric receptor whose extracellular moiety is composed of a humanized scFv derived from the anti-CEA mAb BW431/26 and the CH2/CH3 constant domains of human IgG. The intracellular moiety consists of the gamma-signaling chain of the human Fc epsilon RI receptor constituting a completely humanized chimeric receptor. After transfection, the humBW431/26 scFv-CH2CH3-gamma receptor is expressed as a homodimer on the surface of MD45 T cells. Co-incubation with CEA+ tumor cells specifically activates grafted MD45 T cells indicated by IL-2 secretion and cytolytic activity against CEA+ tumor cells. Notably, the efficacy of receptor-mediated activation is not affected by soluble CEA up to 25 µg/mL demonstrating the usefulness of this chimeric receptor for specific cellular activation by membrane-bound CEA even in the presence of high concentrations of CEA, as found in patients during progression of the disease (Hombach, A., et al., *A chimeric receptor that selectively targets membrane-bound carcinoembryonic antigen (mCEA) in the presence of soluble CEA.* Gene Ther, 1999. 6(2): p. 300-4). These methods are described to guide one of skill in the art to practicing the disclosure, which in one embodiment is the utilization of CAR T cell approaches towards targeting tumor endothelium as comparted to simply targeting the tumor itself.

Targeting of mucins associated with cancers has been performed with CAR T cells by grafting the antibody that binds to the mucin with CD3 zeta chain. In an older publication chimeric immune receptor consisting of an extracellular antigen-binding domain derived from the CC49 humanized single-chain antibody, linked to the CD3zeta signaling domain of the T cell receptor, was generated (CC49-zeta). This receptor binds to TAG-72, a mucin antigen expressed by most human adenocarcinomas. CC49-zeta was expressed in CD4+ and CD8+ T cells and induced cytokine production on stimulation. Human T cells expressing CC49-zeta recognized and killed tumor cell lines and primary tumor cells expressing TAG-72. CC49-zeta T cells did not mediate bystander killing of TAG-72-negative cells. In addition, CC49-zeta T cells not only killed FasL-positive tumor cells in vitro and in vivo, but also survived in their presence, and were immunoprotective in intraperitoneal and subcutaneous murine tumor xenograft models with TAG-72-positive human tumor cells. Finally, receptor-positive T cells were still effective in killing TAG-72-positive targets in the presence of physiological levels of soluble TAG-72, and did not induce killing of TAG-72-negative cells under the same conditions (McGuinness, R. P., et al., *Anti-tumor activity of human T cells expressing the CC49-zeta chimeric immune receptor.* Hum Gene Ther, 1999. 10(2): p. 165-73).

In one embodiment, the ability of immune cells to recognize tumors is utilized for the purpose of identification. Infiltration of immune cells into tumors is a well-known phenomenon and publications are provided to assist one of skill in the art of practicing the disclosure, specifically, characterization of lymphocytic infiltration into tumors has been shown in bowel tumors (Bland, P. W., *The local immune response to large bowel tumors.* Acta Chir Scand Suppl, 1985. 525: p. 70-92), head and neck cancer (Wolf, G. T., et al., *Lymphocyte subpopulations infiltrating squamous carcinomas of the head and neck: correlations with extent of tumor and prognosis.* Otolaryngol Head Neck Surg, 1986. 95(2): p. 142-52; Murali, P. S., et al., *Interleukin-2 mediated regulation of mitogen-activated T cell reactivity from different lymphoid sources in patients with squamous cell carcinoma of the oral cavity.* J Oral Pathol Med, 1989. 18(6): p. 327-32), bladder cancer (Tsujihashi, H., et al., *Immunocompetence of tissue infiltrating lymphocytes in bladder tumors.* J Urol, 1988. 140(4): p. 890-4; Tsujihashi, H., et al., *Immunohistochemical detection of tissue-infiltrating lymphocytes in bladder tumors.* Urol Int, 1989. 44(1): p. 5-9; Tsujihashi, H., et al., *Immunoresponse of tissue infiltrating lymphocytes in bladder tumors.* J Urol, 1989. 141(6): p. 1467-70), glioblastoma (Kuppner, M. C., M. F. Hamou, and N. de Tribolet, *Immunohistological and functional analyses of lymphoid infiltrates in human glioblastomas.* Cancer Res, 1988. 48(23): p. 6926-32; Ebato, M., et al., *Skewed distribution of TCR V alpha 7-bearing T cells within tumor-infiltrating lymphocytes of HLA-A24(9)-positive patients with malignant glioma.* Immunol Lett, 1993. 39(1): p. 53-64) breast cancer (Tsujihashi, H., et al., *Immunohistochemical detection of tissue-infiltrating lymphocytes in bladder tumors.* Urol Int, 1989. 44(1): p. 5-9), melanoma (Topalian, S. L., D. Solomon, and S. A. Rosenberg, *Tumor-specific cytolysis by lymphocytes infiltrating human melanomas.* J Immunol, 1989. 142(10): p. 3714-25; Albertini, M. R., et al., *Analysis of T cell receptor beta and gamma genes from peripheral blood, regional lymph node and tumor-infiltrating lymphocyte clones from melanoma patients.* Cancer Immunol Immunother, 1991. 32(5): p. 325-30), lung cancer (Pisani, R. J., et al., *Lymphokine-activated killer (LAK) cell activity in tumor-infiltrating lymphocytes from non-small cell lung cancer.* Am J Clin Pathol, 1989. 92(4): p. 435-46; Yoshino, I., et al., *Oligoclonal T lymphocytes infiltrating human lung cancer tissues.* Int J Cancer, 1991. 47(5): p. 654-8, stomach cancer (Minamoto, T., et al., *Medullary carcinoma with lymphocytic infiltration of the stomach. Clinicopathologic study of 27 cases and immunohistochemical analysis of the subpopulations of infiltrating lymphocytes in the tumor.* Cancer, 1990. 66(5): p. 945-52), ovarian cancer (Ma, D. and M. J. Gu, *Immune effect of tumor-infiltrating lymphocytes and its relation to the survival rate of patients with ovarian malignancies.* J Tongji Med Univ, 1991. 11(4): p. 235-9; Peoples, G.E., et al., *T-cell recognition of ovarian cancer.* Surgery, 1993. 114(2): p. 227-34; Kooi, S., et al., *Cytokine production by T-cell lines derived from tumor-infiltrating lymphocytes from patients with ovarian carcinoma: tumor-specific immune responses and inhibition of antigen-independent cytokine production by ovarian tumor cells.* Lymphokine Cytokine Res, 1993. 12(6): p. 429-37), and colorectal cancer (Di Giorgio, A., et al., *The influence of tumor lymphocytic infiltration on long term survival of surgically treated colorectal cancer patients.* Int Surg, 1992. 77(4): p. 256-60; Hom, S. S., S. A. Rosenberg, and S. L. Topalian, *Specific immune recognition of autologous tumor by lymphocytes infiltrating colon carcinomas: analysis by cytokine secretion.* Cancer Immunol Immunother, 1993. 36(1): p. 1-8). The citations referred to herein are all incorporated by reference in their entireties.

In some embodiments, tumor infiltrating lymphocytes are extracted according to protocols provided, labelled with a labelling means, and subsequently administered for identification of tumor micrometastasis. The tumor infiltrating lymphocytes may be autologous or allogeneic. In some embodiments, the tumor infiltrating lymphocytes may be augmented by vaccination, as described (Oratz, R., et al., *Induction of tumor-infiltrating lymphocytes in human malignant melanoma metastases by immunization to melanoma antigen vaccine.* J Biol Response Mod, 1989. 8(4): p. 355-8; Steerenberg, P. A., et al., *Tumor infiltrating leukocytes (tils) during progressive tumor growth and BCG-mediated tumor regression.* Virchows Arch B Cell Pathol Incl Mol Pathol, 1990. 59(4): p. 185-94; Sawamura, Y. and N. de Tribolet, *Immunobiology of brain tumors.* Adv Tech Stand Neurosurg, 1990. 17: p. 3-64; Topalian, S. L. and S. A. Rosenberg, *Tumor-infiltrating lymphocytes: evidence for specific immune reactions against growing cancers in mice and humans.* Important Adv Oncol, 1990: p. 19-41). In some embodiments tumor infiltrating lymphocytes may be obtained and cultured from patients that have undergone spontaneous remission (Knisely, T. L. and J. Y. Niederkorn, *Immunologic evaluation of spontaneous regression of an intraocular murine melanoma.* Invest Ophthalmol Vis Sci, 1990. 31(2): p. 247-57; Kitai, H., et al., *Spontaneous regression of small cell lung cancer combined with cancer associated retinopathy.* Lung Cancer, 2015. 87(1): p. 73-6; Bulkley, G. B., et al., *Long-term spontaneous regression of malignant melanoma with visceral metastases. Report of a case with immunologic profile.* Cancer, 1975. 36(2): p. 485-94; Cole, W. H., *Relationship of causative factors in spontaneous regression of cancer to immunologic factors possibly effective in cancer.* J Surg Oncol, 1976. 8(5): p. 391-411; Bodurtha, A. J., et al., *A clinical histologic, and immunologic study of a case of metastatic malignant melanoma undergoing spontaneous remission.* Cancer, 1976. 37(2): p. 735-42; Hellstrom, K. E. and I. Hellstrom, *Spontaneous tumor regression: possible relationship to in vitro parameters of tumor immunity.* Natl Cancer Inst Monogr, 1976. 44: p. 131-4; Firminger, H. I., *A pathologist looks at spontaneous regression of cancer.* Natl Cancer Inst Monogr, 1976. 44: p. 15-8; Hunt, M. J., et al., *Regression in basal cell carcinoma: an immunohistochemical analysis.* Br J Dermatol, 1994. 130(1): p. 1-8; Ferradini, L., et al., *Analysis of T cell receptor variability in tumor-infiltrating lymphocytes from a human regressive melanoma. Evidence for in situ T cell clonal expansion.* J Clin Invest, 1993. 91(3): p. 1183-90; Ishizu, H., et al., *Immune-mediated regression of 'metastatic' neuroblastoma in the liver.* J Pediatr Surg, 1994. 29(2): p. 155-9; discussion 159-60; Abubakr, Y. A., T. H. Chou, and B. G. Redman, *Spontaneous remission of renal cell carcinoma: a case report and immunological correlates.* J Urol, 1994. 152(1): p. 156-7; Mentzer, S. J., *Immunoreactivity in lung cancer.* Chest Surg Clin N Am, 1995. 5(1):

p. 57-71; Zorn, E. and T. Hercend, *A MAGE-6-encoded peptide is recognized by expanded lymphocytes infiltrating a spontaneously regressing human primary melanoma lesion.* Eur J Immunol, 1999. 29(2): p. 602-7; Inoue, T., et al., *Spontaneous regression of merkel cell carcinoma: a comparative study of TUNEL index and tumor-infiltrating lymphocytes between spontaneous regression and non-regression group.* J Dermatol Sci, 2000. 24(3): p. 203-11; Nakai, T., T. Shimomura, and F. Hirokawa, *Spontaneous regression of recurrent hepatocellular carcinoma after TAE: possible mechanisms of immune mediation.* Int J Clin Oncol, 2001. 6(3): p. 149-52; Kawai, K., et al., *Enhancement of T cell proliferative response against autologous cancer cells of a metasatic renal cell carcinoma patient after unexplained regression.* Int J Urol, 2004. 11(12): p. 1130-2; Saleh, F., et al., *Direct evidence on the immune-mediated spontaneous regression of human cancer: an incentive for pharmaceutical companies to develop a novel anti-cancer vaccine.* Curr Pharm Des, 2005. 11(27): p. 3531-43; Hamilton, D. H. and P. A. Bretscher, *Different immune correlates associated with tumor progression and regression: implications for prevention and treatment of cancer.* Cancer Immunol Immunother, 2008. 57(8): p. 1125-36). Furthermore, in some patients spontaneous regression occurs after bacterial or viral infections (Bowles, A. P., Jr. and E. Perkins, *Long-term remission of malignant brain tumors after intracranial infection: a report of four cases.* Neurosurgery, 1999. 44(3): p. 636-42; discussion 642-3), further suggesting immunological causes. In addition to lymphocytic infiltrations, antigen-specific T cells have been detected to be associated with spontaneous regression (Nakamura, Y., et al., *Spontaneous remission of a non-small cell lung cancer possibly caused by anti-NY-ESO-1 immunity.* Lung Cancer, 2009. 65(1): p. 119-22). Studies initiated by Rosenberg's group demonstrated that extraction of tumor infiltrating lymphocytes followed by ex vivo expansion and re-infusion results in substantial tumor regression (Lazarus, D. S., J. T. Kurnick, and R. L. Kradin, *Alterations in pulmonary function in cancer patients receiving adoptive immunotherapy with tumor-infiltrating lymphocytes and interleukin-2.* Am Rev Respir Dis, 1990. 141(1): p. 193-8; Fisher, B., et al., *Tumor localization of adoptively transferred indium-111 labeled tumor infiltrating lymphocytes in patients with metastatic melanoma.* J Clin Oncol, 1989. 7(2): p. 250-61; Hayakawa, K., et al., *Study of tumor-infiltrating lymphocytes for adoptive therapy of renal cell carcinoma (RCC) and metastatic melanoma: sequential proliferation of cytotoxic natural killer and noncytotoxic T cells in RCC.* J Immunother (1991), 1991. 10(5): p. 313-25; Whiteside, T. L., *Cancer therapy with tumor-infiltrating lymphocytes: evaluation of potential and limitations.* In Vivo, 1991. 5(6): p. 553-9; Rosenberg, S. A., *The development of new cancer therapies based on the molecular identification of cancer regression antigens.* Cancer J Sci Am, 1995. 1(2): p. 90-100; Skornick, Y., S. Topalian, and S. A. Rosenberg, *Comparative studies of the long-term growth of lymphocytes from tumor infiltrates, tumor-draining lymph nodes, and peripheral blood by repeated in vitro stimulation with autologous tumor.* J Biol Response Mod, 1990. 9(4): p. 431-8), especially when patients are previously treated by lymphodepletion. In some embodiments, this approach is utilized to generate cells useful for specific recognition of tumors. Augmentation of activity of lymphocyte immunotherapies was observed utilizing chimeric receptors was demonstrated in animal studies, Hwu et al. examined the in vivo activity of murine T cells transduced with a chimeric receptor gene (MOv-gamma) derived from the mAb MOv18, which binds to a folate-binding protein overexpressed on most human ovarian adenocarcinomas. Nude mice that were given i.p. implants of human ovarian cancer (IGROV) cells were treated 3 days later with i.p. murine tumor-infiltrating lymphocytes (TIL) derived from an unrelated tumor. Mice treated with MOv-gamma-transduced TIL (MOv-TIL) had significantly increased survival compared to mice treated with saline only, nontransduced TIL, or TIL transduced with a control anti-trinitrophenyl chimeric receptor gene (TNP-TIL). In another model, C57BL/6 mice were given i.v. injections of a syngeneic methylcholanthrene-induced sarcoma transduced with the folate-binding protein (FBP) gene (Goedegebuure, P. S., et al., *Adoptive immunotherapy with tumor-infiltrating lymphocytes and interleukin-2 in patients with metastatic malignant melanoma and renal cell carcinoma: a pilot study.* J Clin Oncol, 1995. 13(8): p. 1939-49). Three days later, mice were treated i.v. with various transduced murine TIL (derived from an unrelated tumor), followed by low-dose systemic interleukin 2. Eleven days after tumor injection, mice were sacrificed, and lung metastases were counted. In multiple experiments, mice receiving MOv-TIL had significantly fewer lung metastases than did mice treated with interleukin 2 alone, nontransduced TIL, or TNP-TIL. These studies indicate that T cells can be gene modified to react in vivo against tumor antigens, defined by mAbs. This approach is potentially applicable to a number of neoplastic and infectious diseases and may allow adoptive immunotherapy against types of cancer not previously amenable to cellular immunotherapy (Hwu, P., et al., *In vivo antitumor activity of T cells redirected with chimeric antibody/T-cell receptor genes.* Cancer Res, 1995. 55(15): p. 3369-73). Within the context of the current disclosure, this approach may be utilized to generate cells capable of specific tumor recognition. Researchers have attempted to counter the immune system's tolerance to cancer cell antigens by genetically modifying T cells with a chimeric antigen receptor (CAR) via grafting, called CAR-T cells (Jena, B., G. Dotti, and L. J. Cooper, *Redirecting T-cell specificity by introducing a tumor-specific chimeric antigen receptor.* Blood, 2010. 116(7): p. 1035-44). CAR-T have the advantage of not requiring presentation of tumor antigen on MHC since they possess an antibody domain. CAR are usually generated by joining a single chain antibody (scFv) to an intracellular signaling domain, usually the zeta chain of the TCR/CD3 complex. The most recent construction of CARs also contain a co-stimulatory molecule such as CD28 or 41BB that can improve effector cell survival and proliferation (Carpenito, C., et al., *Control of large, established tumor xenografts with genetically retargeted human T cells containing CD28 and CD137 domains.* Proc Natl Acad Sci U S A, 2009. 106(9): p. 3360-5). For cancer therapy, T-CARs have at least three major advantages over natural T cell receptors. First, the antigen binding affinity of scFv is typically much higher than the binding moiety of most TCRs. A high affinity binding is desired for efficient T cell activation. Second, due to the nature of scFv-mediated antigen binding, T-CAR recognition is non-MHC restricted and independent of antigen processing. This widens the use of T-CARs to patients with different MHC haplotypes. Third, because T-CAR recognition is non-MHC restricted, their ability to target cancer cells is not hampered by a cancer cells' ability to down regulate MHC (an important mechanism by which tumor cells evade cancer immunotherapies). CARs have been previously constructed with scFvs that bind to a variety of tumor-associated antigens. Encouraging preclinical data has prompted a series of clinical trials using adoptive transfer of T cells engrafted with these CARs for treatment of tumors having different tissue origins, including melanoma, lymphoma, neuroblastoma, and colorectal cancer. Many of these trials have shown promising results, even complete remission of the established tumors in some cases. The citations referred to herein are all incorporated by reference in their entireties.

In some embodiments, immune cells are labelled with compounds capable of detection intrasurgically, or non-invasively. The immune cells may be labelled by gene manipulation in order to stably express a label, or may be modified by cell painting techniques or other techniques. Compounds useful for labelling immune cells include cyanine compounds having this general form are described for example in U.S. Pat. Nos. 6,995,274, 6,683,188, 6,649,335, 6,437,141, 6,224,644, 6,114,350, 6,197,956, 6,027,709, and 5,268,486, which are each incorporated by reference herein. The cyanine compound fluoresces from about 650 to 900 nm. In some embodiments, a glucose compound is selected from one of the following: glucose and derivatives thereof, D-glucose and derivatives thereof, glucosamine and derivatives thereof. Specifically, the cyanine compound may be attached to the glucose compound by an amide linkage. In other embodiments, Positron-emission tomography (PET) is used to detect labelled immune cells. Tracers such as 2-deoxy-2-($^{18}$F)fluoro-D-glucose (($^{18}$F)FDG) and other radiopharmaceuticals may be used to label immune cells in order to track to tumor tissues. Detection of tumor tissues may be accomplished by cells which specifically possess a proclivity towards tumor tissues. In one embodiment the cells possess a T cell receptor or B cell receptor which recognizes tumor tissues, the receptors may recognize antigens associated with tumors, or antigens associated with tumor vasculature. Tumor endothelial antigens are well known in the art and include Endoglin, (CD105) which is strongly expressed in tumor endothelial cells (Duff, S. E., et al., *CD105 is important for angiogenesis: evidence and potential applications*. FASEB J, 2003. 17(9): p. 984-92). CD105 expression on tumor vessels is a prognostic factor correlated with poor overall and disease-free survival, tumor recurrence, and metastasis of various cancers (Basilio-de-Oliveira, R. P. and V. L. Nunes Pannain, *Prognostic angiogenic markers (endoglin, VEGF, CD31) and tumor cell proliferation (Ki67) for gastrointestinal stromal tumors*. World J Gastroenterol, 2015. 21(22): p. 6924-30; Svatek, R. S., et al., *Preoperative plasma endoglin levels predict biochemical progression after radical prostatectomy*. Clin Cancer Res, 2008. 14(11): p. 3362-6). CD105 vaccination approaches employing bacterial surface display of protein (Huang, F. Y., et al., *Bacterial surface display of endoglin by antigen 43 induces antitumor effectiveness via bypassing immunotolerance and inhibition of angiogenesis*. Int J Cancer, 2014. 134(8): p. 1981-90) and orally administered DNA vaccines (Jarosz, M., et al., *Therapeutic antitumor potential of endoglin-based DNA vaccine combined with immunomodulatory agents*. Gene Ther, 2013. 20(3): p. 262-73) effectively targeted the vasculature and inhibited tumor growth in the absence of observable effects on healthy tissues. Accordingly, in some embodiments, the use of modified immune cells to recognize CD105 is described, specifically, the immune cells "recognizing" or "interacting" with CD105 are modified to produce a signal that can be detected either surgically, or non-invasively. The signal may include a nanoparticle which may be visualized by a visualization means, the signal may include a radioisotope, alternatively, the signal may be genetically engineered into the immune cells such that activation of the immune cells results in production of the signal. Signals may include artificial or non-endogenous compounds whose detection would only be indicative of activation of the immune cell, or recognition of the immune cells of an antigen, in one embodiment the antigen including CD105. It is obvious to one of skill in the art that other antigens may be used as targets of the disclosure, which teaches the use of immune cells as specific agents which seek and identify pathologies in the body. The immune cells may be activated, in the case of T cells, by engagement of the T cell receptor, leading to production of interleukin-2. Accordingly, in one embodiment the interleukin-2 promoter, or target sites of transcriptional machinery associated with TCR engagement are utilized to cause production of genes whose expression leads to detection. In one embodiment the genes include GFP, luciferase, YFP or other fluorescent molecules. In other embodiments the genes cause production of a soluble signal which may be detected, the soluble signal may be non-endogenous to the host. The citations referred to herein are all incorporated by reference in their entireties.

In some embodiments, in which immune cells are desired that selectively home to hypoxic tissues, the immune cells are conditioned by hypoxia before administration, specifically hypoxic conditions can include an oxygen level of lower than 10%. In some embodiments, hypoxic conditions include up to about 7% oxygen. For example, hypoxic conditions can include up to about 7%, up to about 6%, up to about 5%, up to about 4%, up to about 3%, up to about 2%, or up to about 1% oxygen. As another example, hypoxic conditions can include up to 7%, up to 6%, up to 5%, up to 4%, up to 3%, up to 2%, or up to 1% oxygen. In some embodiments, hypoxic conditions include about 1% oxygen up to about 7% oxygen. For example, hypoxic conditions can include about 1% oxygen up to about 7% oxygen; about 2% oxygen up to about 7% oxygen; about 3% oxygen up to about 7% oxygen; about 4% oxygen up to about 7% oxygen; about 5% oxygen up to about 7% oxygen; or about 6% oxygen up to about 7% oxygen. As another example, hypoxic conditions can include 1% oxygen up to 7% oxygen; 2% oxygen up to 7% oxygen; 3% oxygen up to 7% oxygen; 4% oxygen up to 7% oxygen; 5% oxygen up to 7% oxygen; or 6% oxygen up to 7% oxygen. As another example, hypoxic conditions can include about 1% oxygen up to about 7% oxygen; about 1% oxygen up to about 6% oxygen; about 1% oxygen up to about 5% oxygen; about 1% oxygen up to about 4% oxygen; about 1% oxygen up to about 3% oxygen; or about 1% oxygen up to about 2% oxygen. As another example, hypoxic conditions can include 1% oxygen up to 7% oxygen; 1% oxygen up to 6% oxygen; 1% oxygen up to 5% oxygen; 1% oxygen up to 4% oxygen; 1% oxygen up to 3% oxygen; or 1% oxygen up to 2% oxygen. As another example, hypoxic conditions can include about 1% oxygen up to about 7% oxygen; about 2% oxygen up to about 6% oxygen; or about 3% oxygen up to about 5% oxygen. As another example, hypoxic conditions can include 1% oxygen up to 7% oxygen; 2% oxygen up to 6% oxygen; or 3% oxygen up to 5% oxygen. In some embodiments, hypoxic conditions can include no more than about 2% oxygen. For example, hypoxic conditions can include no more than 2% oxygen.

Although radionuclide imaging modalities display some advantages including intrinsically high sensitivity, capability of quantitation, and ability to image a human subject, they often suffer from relatively low spatial resolution, high cost, and significant radiation to personnel. Moreover, imaging probes with a short half-life are needed for PET imaging and for on-site cyclotron and radiochemistry laboratories. Furthermore, the recent emergence of optical imaging (bioluminescence and fluorescence imaging) as imaging modalities to study biological events in vitro and in vivo require new probes that do not involve radiation, and that are inexpensive yet highly sensitive. The acquisition times for optical imaging can be as short as seconds, allowing use of these techniques in high-throughput applications, if suitable probes are developed.

In recent years, the use of near-infrared fluorescent imaging as a diagnostic and detection tool has grown, in part because of the strong tissue penetration ability of light in the near-infrared (NIR) region (650-900 nm wavelengths). Near-infrared imaging is a viable method to non-invasively monitor disease states at a molecular level, to detect localized cancer areas, and to assess antitumor efficacy of therapeutic drugs. There remains a need, however, for compounds suitable for use in near-infrared optical imaging.

In some embodiments, immune cells are labeled with compounds capable of detection by magnetic imaging means; in a specific example immune cells are labeled with gadolinium. In some embodiments, the labeled immune cells localize to altered cells. In some embodiments, detecting altered cells includes the use of an MRI or other magnetic detection device to detect the label.

In some embodiments, immune cells are labeled with compounds capable of detection by sonographic imaging means; in a specific example immune cells are labeled with microbubbles.

In some embodiments, immune cells are labeled with compounds capable of detection by ionizing radiation imaging; in a specific example immune cells are labeled with radiation activatable nanoparticles; in another specific example composition comprising a scintillator nanocrystal linked to a chemical agent moiety through a scintillator-activated photocleavable linker.

In some embodiments, the labeled immune cells localize to altered cells. Thus, in some embodiments, "detecting altered cells" is performed based on the type of label that is used. In some embodiments, detecting altered cells includes the detection of fluorescent labels. In some embodiments, detecting altered cells includes the use of an MRI or other magnetic detection device to detect the label. In some embodiments, detecting altered cells includes the use of ultrasound or other sonographic device to detect the label. In some embodiments, detecting altered cells includes the use of positron emission tomography, radiography, or other radiation imaging device to detect the label.

EXAMPLES

Example 1

CAR T Cell Generation

This example demonstrates the generation of a CAR T cell according to one embodiment.

In some embodiments, FMC63-28z CAR (Genebank identifier HM852952.1), is used as the template for the CAR except the anti-CD19, single-chain variable fragment sequence is replaced with an ROBO-4 fragment. The construct is synthesized and inserted into a pLNCX retroviral vector. Retroviruses encoding the ROBO-4-specific CAR are generated using the retrovirus packaging kit, Ampho (Takara), following the manufacturer's protocol. For generation of CAR-T cells donor blood is obtained and after centrifugation on Ficoll-Hypaque density gradients (Sigma-Aldrich), PBMCs are plated at 2 ×10$^6$ cells/mL in cell culture for 2 hours and the non-adherent cells are collected. The cells were then stimulated for 2 days on a non-tissue-culture-treated 24-well plate coated with 1 µg/mL OKT3 (Biolegend) at 1×10$^6$ cells/mL and in the presence of 1 µg/mL of anti-human CD28 antibody (Biolegend). For retrovirus transduction, a 24-well plate are coated with RetroNectin (Takara) at 4° C. overnight, according to the manufacturer's protocol, and then blocked with 2% BSA at room temperature for 30 min. The plate was then loaded with retrovirus supernatants at 300 µL/well and incubated at 37° C. for 6 h. Next, 1×10$^6$ stimulated PBLs in 1 mL of medium are added to 1 mL of retrovirus supernatants before being transferred to the pre-coated wells and cultured at 37° C. for 2 d. The cells are then transferred to a tissue-culture-treated plate at 1×10$^6$ cells/mL and cultured in the presence of 100 U/mL of recombinant human IL-2 (Deng, Z., et al., *Adoptive T-cell therapy of prostate cancer targeting the cancer stem cell antigen EpCAM*. BMC Immunol, 2015. 16(1): p. 1). Other means of generating CARs are described herein.

Example 2

Method of Detecting Diseased Cells

This example demonstrates the method as described herein for the detection of diseased cells.

A subject having diseased cells is identified. In this example, the subject has melanoma cancer. Melanoma samples are obtained from the subject, including from primary skin lesions or visceral metastases. Tumor samples from the subject are mechanically and enzymatically dissociated and lymphocytes are purified by techniques as known in the art, for example see *Remington: The Science and Practice of Pharmacy* (Easton, Pa.: Mack Publishing Co., 1995), which is incorporated herein by reference in its entirety.

The lymphocytes from the tumors are expanded in culture, using techniques known in the art, for example, see *Remington: The Science and Practice of Pharmacy* (Easton, Pa.: Mack Publishing Co., 1995). The expanded lymphocytes are then labeled with an appropriate label. For example, the lymphocytes may be labeled with a fluorescent label, including, for example, green fluorescent protein (GFP), including, for example, Aequoria victoria GFP, *Renilla muelleri* GFP, *Renilla reniformis* GFP, *Renilla ptilosarcus*, a blue fluorescent protein (BFP), a yellow fluorescent protein (YFP), a red fluorescent protein (RFP), a cyan fluorescent protein (CFP), an orange fluorescent protein (OFP). The label can also include, for example, a reporter gene, including neomycin, phosphoro-transferase, chloramphenicol acetyl transferase, thymidine kinase, β-glucuronidase, aminoglycoside, phosphotransferase, hygromycin B, xanthine-guanine phosphoribosyl, luciferases (e.g., renilla, firefly, etc.), DHFR/methotrexate, β-galactosidase, alkaline phosphatase, turbo and tagRFP, and nuclear targeted versions of any of the aforementioned reporter genes. The label can also include radioactive compounds that may be detected by magnetic imaging means, including $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94}$Tc, $^{94}$Tc, $^{99m}$Tc, $^{120}$I, $^{123}$I, $^{124}$I, $^{125}$I, $^{131}$I, $^{154}$Gd, $^{155}$Gd, $^{156}$Gd, $^{157}$Gd, $^{158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, or $^{83}$Sr, or one or a plurality of quantum dots. The label can also include compounds capable of detection by sonographic imaging means, including, for example, with microbubbles. The label can also include compounds capable of detection by ionizing radiation imaging, including for example, with radiation activatable nanoparticles or a scintillator nanocrystal linked to a chemical agent moiety through a scintillator-activated photocleavable linker.

The labeled lymphocytes are maintained for further use. The subject is monitored, and if a state of remission occurs, or if further studies are warranted, the labeled lymphocytes are administered to the subject by intravenous administration. The labeled lymphocytes localize to the melanoma cells by binding to MAGE antigen, and are detected using an appropriate imaging device, capable of detecting the label.

This example describes the method for the detecting MAGE antigen in a melanoma subject. The steps described in the example can be used in a similar fashion to detect her2/neu antigen in a subject suffering from residual breast cancer, PSMA antigen in a subject suffering from prostate cancer, IDH1 or IL13Rα2 mutation antigen in a subject suffering from brain cancer, or epCAM antigen in a subject suffering from colon, lung, or other epithelial cancers, or other respective antigens in other cancers. In addition, the method can be used for the detection of altered cells in diseases other than cancer, including for example, in cardiovascular disease, viral infections, bacterial infections, or other diseases that present stressed cells.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All patents and publications mentioned in the specification are indicative of the levels of those skilled in the art to which the disclosure pertains. All patents and publications are herein incorporated by reference to the same extent as if each individual publication was specifically and individually indicated to be incorporated by reference.

While the present disclosure has been described in some detail for purposes of clarity and understanding, one skilled in the art will appreciate that various changes in form and detail can be made without departing from the true scope of the disclosure.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present disclosure. This disclosure is susceptible to modifications in the methods and materials, as well as alterations in the fabrication methods and equipment. Such modifications will become apparent to those skilled in the art from a consideration of this disclosure or practice of the embodiments disclosed herein. Consequently, it is not intended that this disclosure be limited to the specific embodiments disclosed herein, but that it cover all modifications and alternatives coming within the true scope and spirit of the disclosure.

The foregoing description and Examples detail certain embodiments. It will be appreciated, however, that no matter how detailed the foregoing may appear in text, the disclosure may be practiced in many ways and the disclosure should be construed in accordance with the appended claims and any equivalents thereof.

EMBODIMENTS

While various aspects and embodiments have been disclosed herein, other aspects and embodiments will be apparent to those skilled in the art. Various example embodiments of the disclosure can be described according to the following embodiments.

Some embodiments disclosed herein related to methods of detecting an altered cell. In some embodiments, the method includes the steps of obtaining a population of immune cells capable of activation subsequent to binding of one or a plurality of antigens found on the altered cell, introducing into the immune cells a means of producing a detectable signal, and c) administering into the individual in which detection of the altered cells is desired the immune cells in a manner allowing for localization of the immune cells to the altered cells. In some embodiments, the altered cell is a preneoplastic cell, a neoplastic cell, a bacterially infected cell, a virally infected cell, a stressed cell, a diseased cell, or an autoimmune cell.

In some embodiments, the population of immune cells is autologous to the recipient. In some embodiments, the population of immune cells is allogeneic to the recipient. In some embodiments, the immune cell is one or more of B cells, T cells, innate lymphoid cells, natural killer cells, natural killer T cells, gamma delta T cells, macrophages, monocytes, dendritic cells, neutrophils, or myeloid derived suppressor cells. In some embodiments, the B cells are either CD5+ B cells or CD5− B cells. In some embodiments, the B cells are either naïve B cells or memory B cells. In some embodiments, the T cells are either CD4+ or CD8+ T cells. In some embodiments, the T cells are CD28 positive or CD28 negative T cells. In some embodiments, the T cells are either memory T cells or naïve T cells. In some embodiments, the T cells are cells that express CD3. In some embodiments, the T cells are T regulatory cells. In some embodiments, the T regulatory cells express one or more of CD25, CTLA-4, or FoxP3.

In some embodiments, the innate lymphoid cells include innate lymphoid cells 1, innate lymphoid cells 2, innate lymphoid cells 3, or lymphoid tissue inducer cells. In some embodiments, the innate lymphoid cell 1 express T bet and respond to IL-12 by secretion of interferon gamma, however lack expression of perforin and CD56. In some embodiments, the innate lymphoid cell 2 produce IL-4 and IL-13. In some embodiments, the innate lymphoid cell 3 produce IL-17a and IL-22. In some embodiments, the lymphoid tissue inducer cells are cells involved in the induction of memory T cells. In some embodiments, the T cells are Th1 cells. In some embodiments, the Th1 cells are capable of secreting cytokines including interferon gamma, interleukin 2, or TNF-beta. In some embodiments, the Th1 cells express markers including CD4, CD94, CD119 (IFNγ R1), CD183 (CXCR3), CD186 (CXCR6), CD191 (CCR1), CD195 (CCR5), CD212 (IL-12Rβ1&2), CD254 (RANKL), CD278 (ICOS), IL-18R, MRP1, NOTCH3, or TIM3. In some embodiments, the T cells are Th0 cells. In some embodiments, the T cells are Th2 cells. In some embodiments, the Th2 cells are capable of secreting cytokines including IL-4, IL-5, IL-6, IL-9, IL-10, or IL-13. In some embodiments, the Th2 cells express markers including CRTH2, CCR4, or CCR3. In some embodiments, the macrophages are M1 or M2 macrophages. In some embodiments, the M1 macrophages are capable of producing nitric oxide. In some embodiments, the M2 macrophages are capable of producing arginase. In some embodiments, the dendritic cells are myeloid dendritic cells or lymphoid dendritic cells. In some embodiments, the myeloid dendritic cells are capable of stimulating Th1 immune responses in a mature state. In some embodiments, the myeloid dendritic cells in the mature state express substantially higher levels of CD80 as compared to myeloid dendritic cells in an immature state. In some embodiments, the myeloid dendritic cells in the mature state express substantially higher levels of CD86 as compared to myeloid dendritic cells in an immature state. In some embodiments, the myeloid dendritic cells in the mature state express substantially higher levels of CD40 as compared to myeloid dendritic cells in an immature state. In some embodiments, the lymphoid dendritic cells are capable of producing interferon alpha.

In some embodiments, the antigen found on altered cells is an antigen associated with cellular proliferation in cells which physiologically should not be proliferating significantly. In some embodiments, the antigen found on altered cells is an antigen associated with cancer. In some embodiments, the antigen found on altered cells is an antigen associated with cancer. In some embodiments, the antigen found on altered cells is an antigen associated with cells exposed to stressors. In some embodiments, the antigen found on altered cells is associated with viral infection. In some embodiments, the antigen found on altered cells is associated with bacterial infection. In some embodiments, the antigen associated with cancer is the protein or peptide derivative of a tumor associated antigen. In some embodiments, the antigen is one or more of CLPP, 707-AP, AFP, ART-4, BAGE, MAGE, GAGE, SAGE, b-catenin/m, bcr-abl, CAMEL, CAP-1, CEA, CASP-8, CDK/4, CDC-27, Cyp-B, DAM-8, DAM-10, ELV-M2, ETV6, G250, Gp100, HAGE, HER-2/neu, EPV-E6, LAGE, hTERT, survivin, iCE, MART-1, tyrosinase, MUC-1, MC1-R, TEL/AML, or WT-1.

In some embodiments, the means of generating a detectable signal upon activation of the is a gene element which encodes a molecule or series of molecules that are secreted and can be detected in systemic circulation of the patient. In some embodiments, the gene element is activated by a promoter associated with activation of the immune cell. In some embodiments, the promoter is activated as a consequence of T cell receptor signal transduction when the immune cell is a T cell. In some embodiments, the promoter is activated as a consequence of B cell receptor signal transduction when the immune cell is a B cell. In some embodiments, the promoter is activated as a consequence of B cell receptor signal transduction when the immune cell is a B cell. In some embodiments, the promoter is activated as a consequence of NK activator receptor when the immune cell is a NK cell. In some embodiments, the promoter is activated as a consequence of NKG2D when the immune cell is a NK cell.

In some embodiments, the promoter is activated by a receptor of a danger associated molecular pattern (DAMP) when the immune cell one or more of macrophages, monocytes, dendritic cells, neutrophils, or myeloid derived suppressor cells In some embodiments, the DAMP receptor is one or more of a toll like receptor (TLR), a receptor for advanced glycation end products (RAGE), a siglec receptor, a stimulator of interferon genes (STING), a retinoic acid-inducible gene I (RIG-I), a melanoma differentiation-associated gene 5 (MDA5), or a Toll-interleukin 1 receptor domain (TIR)-containing adapter molecule 1 (TICAM-1).

In some embodiments, the promoter is activated by a PAMP receptor of a pathogen associated molecular pattern (PAMP) when the immune cell is one or more of macrophages, monocytes, dendritic cells, neutrophils, or myeloid derived suppressor cells. In some embodiments, the PAMP receptor is one or more of a toll like receptor (TLR), a receptor for advanced glycation end products (RAGE), a siglec receptor, a stimulator of interferon genes (STING), a retinoic acid-inducible gene I (RIG-I), a melanoma differentiation-associated gene 5 (MDA5), or a Toll-interleukin 1 receptor domain (TIR)-containing adapter molecule 1 (TICAM-1).

In some embodiments, the immune cell is immortalized. In some embodiments, the immune cell is tagged ex vivo with an agent allowing for in vivo localization. In some embodiments, the agent allows for in vivo localization is $^{111}$In. In some embodiments, the agent allows for in vivo localization a quantum dot. In some embodiments, the agent allows for in vivo localization is $^{99}$Tc. In some embodiments, the immune cell is engineered to express a molecule binding with sufficient affinity to the altered-cell associated protein in order to induce an activation even in the immune cell. In some embodiments, the immune cell is a chimeric antigen receptor T cell.

In some embodiments, the means of generating a detectable signal upon activation of the immune cell is a gene element which encodes a molecule or series of molecules whereby the cells can be detected in systemic circulation of the patient. In some embodiments, the immune cells are generated with a means of clearing, eliminating, or killing the altered cell being detected. In some embodiments, the means of clearing, eliminating, or killing the altered cell is an inducible construct causing expression of a cytotoxic gene product. In some embodiments, the cytotoxic gene product includes one or more of TNF-alpha, TNF-beta, TRAIL, FasL, perforin, or granzyme.

In some embodiments, the administration of the immune cell includes a means of clearing, eliminating, inactivating, or killing the immune cell. In some embodiments, the immune cell is generated so as to be activatable in a non-permissive environment. In some embodiments, the antigen associated with cancer the protein or peptide derivative of a cancer testis antigen. In some embodiments, the antigen associated with a disease state.

What is claimed is:

1. A method of in vivo labeling a melanoma cell in an individual having melanoma cancer, the method comprising the steps of:

obtaining a population of lymphocytes capable of activation subsequent to binding to an antigen on the melanoma cell;
   labeling the population of lymphocytes with a label capable of producing a detectable signal;
   administering to the individual the labeled population of lymphocytes; and
   detecting the melanoma cell with the labeled population of lymphocytes in vivo.

2. The method of claim 1, wherein the population of lymphocytes is autologous to the individual.

3. The method of claim 1, wherein the population of lymphocytes is allogeneic to the individual.

4. The method of claim 1, wherein the antigen on the melanoma cell is an antigen associated with melanoma cancer.

5. The method of claim 4, wherein the antigen is one or more of CLPP, 707-AP, BAGE family, BING-4, melanoma associated antigen (MAGE) family, CTL-recognized antigen on melanoma (CAMEL), EphA3, Gp100, HAGE, survivin, melanoma antigen recognized by T cells (MART-1), tyrosinase, MC1-R, preferentially expressed antigen in melanoma (PRAME), Ig, TCR, epCAM or WT-1.

6. The method of claim 1, wherein the label is a reporter gene selected from the group consisting of neomycin, phosphoro-transferase, chloramphenicol acetyl transferase, thymidine kinase, β-glucuronidase, aminoglycoside, phosphotransferase, hygromycin B, xanthine-guanine phosphoribosyl, luciferase, DHFR/methotrexate, β-galactosidase, alkaline phosphatase, turbo and tagRFP, or nuclear targeted versions of the same.

7. The method of claim 1, wherein the population of lymphocytes is immortalized.

8. The method of claim 1, wherein the population of lymphocytes is tagged ex vivo with an agent allowing for in vivo localization.

9. The method of claim 8, wherein the agent is a radiolabel imaging agent, therapeutic agent, or diagnostic agent selected from the group consisting of $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94}$Tc, $^{94}$Tc, $^{99m}$Tc, $^{120}$I, $^{123}$I, $^{124}$I, $^{125}$I, $^{131}$I, $^{154}$Gd, $^{155}$Gd, $^{156}$Gd, $^{157}$Gd, $^{158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, or $^{83}$Sr, or one or a plurality of quantum dots.

10. The method of claim 1, wherein the melanoma cancer is Harding-Passey melanoma, juvenile melanoma, lentigo maligna melanoma, malignant melanoma, acral-lentiginous melanoma, amelanotic melanoma, benign juvenile melanoma, Cloudman's melanoma, S91 melanoma, nodular melanoma subungal melanoma, or superficial spreading melanoma.

11. The method of claim 1, wherein the population of lymphocytes is obtained from a melanoma cancer sample obtained from the individual.

12. The method of claim 11, wherein the melanoma cancer sample is a primary skin lesion or a visceral metastasis.

13. The method of claim 1, wherein the label is a fluorescent label selected from the group consisting of green fluorescent protein (GFP), blue fluorescent protein (BFP), yellow fluorescent protein (YFP), red fluorescent protein (RFP), cyan fluorescent protein (CFP), or orange fluorescent protein (OFP).

14. The method of claim 1, wherein the label is a microbubble, radiation activatable nanoparticle, or scintillator nanocrystal linked to a chemical agent moiety.

15. The method of claim 1, wherein the labelled population of lymphocytes localizes to melanoma cells by binding to a melanoma associated antigen.

16. The method of claim 1, wherein detecting comprises measuring the detectable label using an imaging device.

* * * * *